(12) United States Patent
De Backer et al.

(10) Patent No.: US 7,572,885 B2
(45) Date of Patent: Aug. 11, 2009

(54) ISOLATED GAGE-7B AND 8 PROTEINS

(75) Inventors: Olivier De Backer, Brussels (BE); Benoit Van den Eynde, Brussels (BE); Thierry Boon-Falleur, Brussels (BE)

(73) Assignee: Ludwig Institute For Cancer Research, New York, NY (US)

( * ) Notice: Subject to any disclaimer, the term of this patent is extended or adjusted under 35 U.S.C. 154(b) by 487 days.

(21) Appl. No.: 10/271,617

(22) Filed: Oct. 16, 2002

(65) Prior Publication Data
US 2003/0157651 A1 Aug. 21, 2003

Related U.S. Application Data

(62) Division of application No. 09/163,748, filed on Sep. 30, 1998, now Pat. No. 6,509,172.

(51) Int. Cl.
*C07K 5/00* (2006.01)
*A61K 38/00* (2006.01)

(52) U.S. Cl. .............. 530/350; 536/23.1; 536/23.5; 514/12

(58) Field of Classification Search .............. None
See application file for complete search history.

(56) References Cited

U.S. PATENT DOCUMENTS

| | | | |
|---|---|---|---|
| 5,610,013 A | 3/1997 | Van dem Eynde et al. | |
| 5,648,226 A | 7/1997 | Van den Eynde et al. | |
| 5,858,689 A | 1/1999 | van der Bruggen et al. | |
| 6,013,481 A | 1/2000 | DeBacker et al. | |
| 6,069,001 A | 5/2000 | Van den Eynde et al. | |
| 6,939,707 B2 | 9/2005 | van der Bruggen et al. | |

OTHER PUBLICATIONS

Fu L. et al. EMBO Journal 15:4392-4401, 1996.*
Powell H. et al. Pharmacogenetics 8(5):411-421, 1998; Abstract only enclosed.*
Vallejo C.G. et al. Biochimie 82(12): 1129-1133, 2000; Abstract only enclosed.*
Jang A et al. Clin. Exp. Metastastis 15(5): 469-483, 1997; Abstract only enclosed.*
DeBacker et al. Cancer Research 59, 3157-3165, 1999.*
Cilensek et al. Cancer Biology & Therapy 1(4): 380-387, 2002.*
Oltra et al. Oncology Research 14: 291-295, 2004.*
Chen et al. Journal of Biological Chemistry 273(28): 17618-17625, Jul. 10, 1998.*
Chen et al.. "Isolation and Characterization of PAGE-1 and GAGE-7," J. Biol. Chem 273 (28): 17618-17625 (1998).
Akcakanat, et al., Heterogeneous expression of GAGE, NY-ESO-1, MAGE-A and SSX proteins in esophageal cancer: Implications for immunotherapy, Int. J. Cancer, 118: 123-128 (2006).

* cited by examiner

*Primary Examiner*—Sheela J Huff
(74) *Attorney, Agent, or Firm*—Fulbright & Jaworski LLP

(57) ABSTRACT

The invention relates to new members of the GAGE family referred to as GAGE-7B and GAGE-8. There are differences between these two molecules and the previously described members of the GAGE family on the genomic DNA, complementary DNA, and amino acid level.

13 Claims, No Drawings

SEQUENCE LISTING

<160> NUMBER OF SEQ ID NOS: 27

<210> SEQ ID NO 1
<211> LENGTH: 528
<212> TYPE: DNA
<213> ORGANISM: Homo sapiens
<220> FEATURE:

<400> SEQUENCE: 1

```
ctgtgaggca gtgctgtgtg gttcctgccg tccggactct ttttcctcta ctgagattca    60
tctgtgtgaa atatgagttg gcgaggaaga tcgacctatc ggcctagacc aagacgctac   120
gtagagcctc ctgaaatgat tgggcctatg cggcccgagc agttcagtga tgaagtggaa   180
ccagcaacac ctgaagaagg ggaaccagca actcaacgtc aggatcctgc agctgctcag   240
gagggagagg atgagggagc atctgcaggt caagggccga agcctgaagc tgatagccag   300
gaacagggtc acccacagac tgggtgtgag tgtgaagatg gtcctgatgg gcaggagatg   360
gacccgccaa atccagagga ggtgaaaacg cctgaagaag gtgaaaagca atcacagtgt   420
taaaagaaga cacgttgaaa tgatgcaggc tgctcctatg ttggaaattt gttcattaaa   480
attctcccaa taaagcttta cagccttctg caaagaaaaa aaaaaaaa                528
```

<210> SEQ ID NO 2
<211> LENGTH: 526
<212> TYPE: DNA
<213> ORGANISM: Homo sapiens
<220> FEATURE:

<400> SEQUENCE: 2

```
tggttcctgc cgtccggact cttttcctc tactgagatt catctgtgtg aaatatgagt    60
tggcgaggaa gatcgaccta ttattggcct agaccaaggc gctatgtaca gcctcctgaa   120
atgattgggc ctatgcggcc cgagcagttc agtgatgaag tggaaccagc aacacctgaa   180
gaagggaac cagcaactca acgtcaggat cctgcagctg ctcaggaggg agaggatgag    240
ggagcatctg caggtcaagg gccgaagcct gaagctcata gccaggaaca gggtcaccca   300
cagactgggt gtgagtgtga agatggtcct gatgggcagg gatggacccc gccaaatcca   360
gaggaggtga aaacgcctga agaaggtgaa aagcaatcac agtgttaaaa gaaggcacgt   420
tgaaatgatg caggctgctc ctatgttgga aatttgttca ttaaaattct cccaataaag   480
ctttacagcc ttctgcaaag aaaaaaaaaa aaaaaaaaa aaaaaa                    526
```

<210> SEQ ID NO 3
<211> LENGTH: 9531
<212> TYPE: DNA
<213> ORGANISM: Homo sapiens
<220> FEATURE:
<221> NAME/KEY: unsure
<222> LOCATION: 92,232,1041,7412,9038-9040
<223> OTHER INFORMATION: identity of several nucleotides not known

<400> SEQUENCE: 3

```
gagctcgctg cagccttgac ctcctgggct caagcgctcc tcccacctca gcctcctgag    60
tagctgtgag tataggtaca tgccaccatg cncagctaat ttttcgatgg ttttttttgtt   120
tgttttttgt agtgatgaga ttttctgatg ttgcttaggc tggtctcgaa gtcctgagct   180
caggtgatct ggccagctca gcctcccaaa atactaggat tacaggcgtg anttggcctg   240
gtctggtttt tcttatatag gggtcttatc tatataaaga ctaaagttaa tctgtgcctt   300
tgtgcgggtg ggctaagagc atgatgactt ttatcattct attgatttaa agaaaactgt   360
ccttgactta ccagtgtgta agtccatgaa agcataattc tgttgaaagc atatattgtt   420
aatgggtgtt gggaaccgtg cactttccgc tgctgtggga gcatgtcctt ggaggtacct   480
ttcatctgtt ttctcaactc caaacatctt aggaccatgg gttgtgactg gtaggactat   540
gtatcttgct gctttcaaga cggagtatat tttcacgtgg tgtcactctg gctgtcctgt   600
ttccctaata ctgtcacttc accctctgcg attctgatgc tacaaatgat agatatcgtt   660
ttagcatttt cttacgggtc ctagcgattc tattcatttt tctttcagtc tctttctctg   720
acttgttcac attgaacaat ttccttttgg gataggttgc tatttctgtt ttcgcaggtg   780
gtttacctgt cttcccagcc agtcacagtg gtccttgtcc ccatggtggg tccggggcaa   840
gagagggccc tgggttgggg gtggggttca gttgaagatg gggtgagttt tgaggggagc   900
actacttgag tcccagaggc ataggaaaca gcagagggag gtgggattcc cttatcctca   960
atgaggatgg gcatggaggg tttggggcgt ggcgctggga acggcagccc tccccagccc  1020
acagccgcgc atgctccctg ntcccgcctc agtgcgcatg ttcactgggc gtcttctgcc  1080
cggcccttc gcccacgtga agaacgccag ggagctgtga ggcagtgctg tgtggttcct   1140
gccgtccgga ctcttttcc tctactgaga ttcatctggt aggtgtgcag gccagtcatc   1200
ccgggggctg aagtgtgagt gagggtggag agggcctcgg gtgggtcagg cgggtccgtt   1260
cctggtctgt ggcctccgag ggagaagggc cacgaggtta cgtacctcct tacccttcac  1320
aggctgcgag gccaccggcg gcttcgtggt cgtgaagggg cctggacggg gaggaaggtg  1380
```

```
ggccgtggag gggaggctgt caggggctca ggtgaagacg gggtgagtgc tgttgggggg   1440
atggaagtcc cgaggtgccg ggatccccga cgacacaggg cagattccct gaatgggccc   1500 ggcggggcg aggcggcgg tgaagaaggg gcctggcacc tgggaaggct gcggcctggc    1560
gagcgccccc cccagcggtg tggagtgcgg agcgcccgag tgagaagcac tgcaaggtct   1620
cacctccgcc atggaaggtc cgaaaacagt gggaaggagt gggcgaggca gtgcggtcca   1680
accaaacttg ttgtgagggg gggtgaatgg ctctaggaag tgggagtgtg cccaaagcag   1740
caatcacgag aattgtgatt cactagggtt ttcgtgggga gtgcacttgt gaaactaaac   1800
ctcatcagaa atgacctctg tctgcggggc gcagtggcgc tcgcctacgt agtcccagtt   1860
actggggaca ctgaggtggg aggatcccctt gagcgggagg tcgaggctgc agtgagctgt   1920
gatcacgccg ctgcactcca gcctgagcaa cacagcgata ccgcgtgtcc aaaagaaatt   1980
tagaaaaaaa tgtcctctgc cttttgccac acgccttaag atgattgctc tgccagcctg   2040
gccagcagaa gtggctttgt aggcactcag acagcgtaca cacgtatgct taactctggg   2100
acttattttg agagtatttt caaaagtaaa acggcaagtt aacatttatc catggaagtg   2160
atcgaatata gcagccctgt ggagcgcacg ttcccaatca cggttgtctg ttttcagtgt   2220
gaaatatgag ttggcgagga agatcgacct attattggcc tagaccaagg cgctatgtac   2280
agcctcctga aatgattggg cctatgcggg tgagtgctta aacgtaatt cgatgttttc    2340 tattagtaga aattaatttt tgtgatagcg tcgttgcatt agtgtggaaa tgctgataaa   2400
ggtctttcct gctcataaaa aatgaggatg gcatctcatg aaggaaacat tgattctgga   2460 ggatttttt ttttcctctc gtgttcttca gcttttgccc atgacttctt tctccggctt    2520
tgtttgttaa tgacagattg tacacatgta ttccaacaca gagtataata gcccccaaag   2580
tcctcgtgcg tcacttttct cacagtaacc tccctgtggg tggagtaacc ttattgggca   2640
tagagcatag agttggagaa atgtctttag gcttagttag gaccagaaat agctatgtat   2700
tctgtgtata tatgtaaaat tttgtatcaa taacgaaact tatttttat ttgcacaccc    2760 acacgtattc cccagcccga gcagttcagt gatgaagtgg aaccagcaac acctgaagaa   2820
ggggaaccag caactcaacg tcaggatcct gcagctgctc aggagggaga ggatgaggga   2880
gcatctgcag gtcaaggtga gggaaaggga agaagaacgt ctgctggtgt gtgcgtgtgt   2940
gtgtgttcgt gtgtgtgtgt gcacgtgtgt gtgtgttagg cattgtcaca taggaggaag   3000
aggaggaaag aaaacaatgg aaagaatgcc tgaaattgac tggaaaagcg aggaggctat   3060
gtagtttgca gcttagctta ggcaaatccc tcactatgat aaaagttctc gactttatga   3120
atgagagaat ggaggtgcca ggattgtgtg ttatccaaga acccttgact ggtgaataca   3180
acatttgtac tgtgttctaa ggtttgtgtc ttcctatcat gtatgttgct ggaaagaagg   3240
aagtgatttt gctgaaaatg cttaaaactc aaaaggcttt actgtaaggt agcttagtac   3300
tgacccaaga atagacccag ttcagaggag caggagcagc tccaaaaacc gagtcgctga   3360
atgttggccc ccgtttcctt tgattgatat ttttatatgg tacgtttgat aaaagctgga   3420
taaatgagga tactgccata caggtagctg gtttagtgat ttttctcagc ggcctttagg   3480
aggtgattaa atccttttat ggttagaaaa gcaaaacgg aattatcctg agattaacgt    3540 gagatgaaa taatttctcc gagataaaat gttttgaaag gaagcattta tgtaacggag   3600
gtcatggatt attccaggga tgcactgtta aaagttccta gaatctgact gacaacaatg   3660
cccattaatt gctgtccgcc cactcctta ttctcagtgc ggggacagta tattttctgt    3720
gattcacaaa caatgttata tttggtgctt tgttcttcac ggggttcatt tatggaatat   3780
```

```
taccttagg accttcggac ctaaatataa ctttatttga acaaagtgaa gtttctcttt    3840 acccccgatag gtaatgggtg tcgtgactgt aagatttcca tagtcctcaa atccatccag   3900
ctaatcaatc cttcagaaac tgacattgta attgtaactg aaatcctacc cacgtggtag   3960
acttcagatt tctcagctga cacacactgc tgttggtact ctagggctga atataagcat   4020
tatacatgtc ctgtggttta tccttagatt gtcatttagg agaaaggtct aaagctgggc   4080
tgaatgccat gcactcatag tcccagctac ttgggaggcc gaggtgagag gattgcttga   4140
gtcctggagt tcaagcccag cctgggaaac acagtgagac ctcattgcta ataaataaat   4200
aaatgaataa ataaataaac acataaataa attcattaaa taaataaagt tttcatggta   4260
taggaaaaca cagatgcaaa gttttttgtgc ctagtggctg gtaatgttgc aaacgtaact   4320
ccttagtgaa ctgtaccact ttagttaaga tggtaaattt taggatatct gtatttttta   4380
ccacaattgg aaattccttt cttcctaaag ttcagtgcag ttatcatata ttcttttaaa   4440
tttttactgt atgtatcttc aagacataac attcatagaa aatttgcaca gaatagtaca   4500
atgaactcat atactgttca tctgattca ccaattgtta gtagcctttc gcttcatagg    4560
tttcacatct cttccctccg tctcttaccg tgctgcccac acactcacac acacacactc   4620
acacacacat acggatatat gtttactgtt attaatgctg aattgtctcg ataaagtttc   4680
agggattatg gtcctttacc ctatgtactt gagggtgtgt atatcgtcag aacaaagaga   4740
aagtcatttc ttggatcatc actgcacaaa gataaaaatc aggaaattta acaatgagaa   4800
aatggagtca tttaatcaca gagtgcatac tcaaattttc ccagttcccc agaaaatttc   4860
ttttttcctt ttttttttct tgttgagac ggagtctccc tctgtgggcc aggttggagg    4920
gcagtagtgc gatctcggct cactgcaacc tacacctccc aggttctagg gattctcatg   4980
cctcagcctc ccgtgtagct gggactacag gcgccggcca ctgcggtctt gaacttctgg   5040
cctcacctgc tctgcccacc ttggcatccc aaaatgtttg gattgcaggc gtgagacccc   5100
acgcccggcc cagataattt tattgatagg atttcttttt ctgatccaga gtccagttga   5160
gaatcacacc ttgcatgtgc ctttcaggtg tttttagttt cctttaacct gtaatgtttc   5220 cttaatttt cttgtcattc acgatacgga catttttgga gaggatagac cagttggttt    5280
gcagaatatt ctgtagtttg ggcttttttca tgtattttt aaaagagttt tctcactcag    5340
cgtttattgg tggctactca tgccatgtaa gagtctaagc gctaggagtg taagtgctgt   5400
gagagacggg atttgagcct tgagtcattt aatacgagaa ggacaatcag aagtagaata   5460
agagagaagt gcaaaggagg cagcaaagtt gtctgagggc agtcttcgga aaggaggagg   5520
gtaatatttc gaacaccttg ttttcctgtt ttctgctaac ggactcctga ataatgttc    5580 ctgggattct tatcaacaca tttattatta cgttagctaa agctctttat ataataatac   5640
cgagagcatg aatatcattt tcttattcat attttatgtt ttactgctta aattgatacg   5700 tatttttat ttttaagggc cgaagcctga agctcatagc caggaacagg gtcacccaca    5760
gactgggtgt gagtgtgaag atggtcctga tgggcaggag atggaccgc caaatccaga    5820 ggaggtgaaa acgcctgaag aaggtaggca atccattagg catgcacatt gtagggtgtc   5880
tgtttccaca gtatcatatt gtaactctta ctatgttttt gagacggagt ctcgctctga   5940
agaccaggct ggagtgcagt ggtgccatct cggctcactg gaaattctgt ctccagggtt   6000
caagtgattc tcctgcctga gcctctggcg gagccgggct tacaggcatg ctccgccgcg   6060
cccagctaat tgttgtattt ttagtagaga cagggtttcg ttatgttgca caggttgttc   6120
```

-continued

```
ccgaactcct gacctcaggt gatccacctg cctcgaccat tgaaattgcc gggattacag    6180
gcagagccac cgtgcccgac ccagcattat attttttaata acagagaggt aacaatactg    6240
cgtctttagt aacagagttc ttatataaag gttatttgaa acgtagttca ggccccagca    6300
cccggctgat agactgtcag atagggaaac aaagtgagtc aaagctatgt tgaattaaaa    6360
gttttgagta taaatcctta aaccagtagc tcacaatttt cagatgcttt tgtaaaggtc    6420
tgcttttaat caatacataa cacgtttgta acacccatca cttggtgtga aaaatgctga    6480
agcactcatg cgggttctaa taccagctct tacagccttg gcgagattct gagtgagtcc    6540
tttcccttct aaacctatct ttggttctta tgaaaatagt gagtttaagt cagagacttt    6600
aaaaccattt tgcattccgt ttctttcata ctctgatcct gttgcataga atgcgtggga    6660
cacagagatc atctcttcgc atggtttgtt aatcacaaat catgaaaccc tggcccgagt    6720
catctgaaaa tctctgaatt gagatttcat tgtcagtaag acagtgagcg ggccctctgc    6780
ttcatcctag ttttttccgtg tggagagctg aatacgtagt ataagatctt gtgaaattgt    6840
gaattctccc tcttcttggt ttgtttgttt gtttgcgaca gagtctcagt gtgtcaccca    6900
ggctggagtg cagtgatgca atttcagctc actgcaactt ctggctccca gctaaagccg    6960
tcctcccacc tcagcctccc gagtggctgg aactacatgc acaagccacc gtgcctgact    7020 acatttttttt gttttcattt ttgtagagat gaggtctcac tgtgttgccc aggcagggtt    7080
tctctggctt ttaatgaaca attgcttctt tttttttcctt ttatttatttt attatacttt    7140 aagtttttagg gtacatgtga cgttgtgcag gttagttaca tacgtataca tgtgccatgc    7200
tgtgcgctgc acccactatc tcatcatcta gcattaggta catctcccag tgctatccct    7260 ccccccctccc cccacccgac aacagtcccc agggtgtgat attccccttc ctctgtccat    7320
gtgatctcat tgttcagttc ccacctatga gtgagaatat gcggtgtttg gtttttttgtt    7380 cttgcgatag tttactgaga atgatgattt cnagtttcat ccatgtccct acaaaggaca    7440
tgaactcttc atttttttagg gctgcatagt attccatagt gtatatgtgc cacatttttct    7500 taatccagtc tatcgttgtt ggacatttgg gttggttcca agtctttgct atcgtgaata    7560
atgccgcaat aaacatacgt gtgcacgtgt ctttatagca gcatgattta tagtcctttg    7620
ggtatatacc cagtaatggg atggctgggt caaatggtac aattgcttct taaatctttc    7680
cccacggaaa ccttgagtga ctgaaataaa tatcaaatgg cgagagaccg tttagttcgt    7740
atcatctgtg gcatgtaggt cagtgatgct cagcatgggt gtgagtaaga tgcctgtgct    7800
atgcatgctc cctgccccac tgtcagtctt catgagccca tatttctaat aagactgtag    7860
acacacatac gatataatca tctctaatca tatcaaatgt tacatgtaag tttcagcttt    7920
agagacatga attgataaga tttaaagttg aaagaccatg actctagtac ttcctgagta    7980
atcaactgaa gtatgcttta cacatgtgtt ttccaaattg ctgactgtta attgtaagtg    8040
cttgtgactt gaaaggaagc acatgatgtt cagggaggaa attcctttta aattctgcag    8100
gtctacgctc aaagtttatg cagaggttca attgcgtgta agacacggga tcacccatag    8160
ggttctgttt ttagtccatt taataaaacc caaactgtag tgtgctttgt atgcctttag    8220
ggtcatctga ataatctgtt gctaagtcat gttcccaatc gttgtgtttc tgttacaggt    8280
gaaaagcaat cacagtgtta aagaaggca cgttgaaatg atgcaggctg ctcctatgtt    8340
ggaaatttgt tcattaaaat tctcccaata aagctttaca gccttctgca aagaagtctt    8400
gcgcatcttt tgtgaagttt atttctagct ttttgatgct gtgaaatatg tatcattctt    8460
tgaaatcgtg tattgtaact ctctgagctg gtatgtagag acatcgttct tttttttttt    8520
```

-continued

```
ctttctttct tgtcctctt ttgagacgga gtcttgctct gtcgcccagg ctggagtgca      8580
gtggcgcgat ctctgctcac tgcaaccccg cctcccggat tcaagcaatt gtctgcctca      8640
gcctcccgag tagctgggat tataggcacc caccagcacg ccctggctaa gttttgtgtt      8700
tttactagag atggtttcgc atcttggccg gggtgctctt gaactcctga cctcgtgatt      8760
cacctgcctt ggcctcccaa agtgctggga ttacaggcat gcacgcctcc gcgcccggtg      8820
gagacataat tcttacatat tggttttcta tccagcggcc ttgtgaaata tgcttgtgaa      8880
ttctaaagtt tacttctagg tcgttttcag tcttcaatat acagaaacat atcatcctgg      8940
aataagagca gttttgtttc cgccattttt ttttgttttt cctttttgtac ttttttttgta   9000 gagacggggt tttgccatgt ttcccgggct gttgttgnnn ttttgagtgc aagtgatgca      9060
cccacgtcac ctcccacagt gctgggatta ctggcgtggg ccaggggcca cccgtggcgg      9120
gccccgtcgt tgccattgta aagagtttta tttcctttc tgattttatg gcattgcgca       9180
gacccacccg ttacaatggt gacagtggac atccttgtct tatccctgat gagaaaccga      9240
aaaatttcaa catttcgcca tcctattcac tctccttttt ttgtagacgg acttatcag       9300 agtgagtcat tgcattctgt tccaaatttg ctgagagtat tcatttgaat atatgttgat      9360
tttcatcaaa cagtgcatct atttcgatta ccacagcgtt ttttcccatt catgggttaa      9420
tatagtgaat tcgattgata aatttgtacg ttttaggtt cgattattaa aacttgagac       9480
agcgtctcac tctgtcaccg aggctggagt gcggtggtgt tatcagagct c               9531
```

<210> SEQ ID NO 4
<211> LENGTH: 18
<212> TYPE: DNA
<213> ORGANISM: Homo sapiens
<220> FEATURE:

<400> SEQUENCE: 4
gaccaagacg ctacgtag                                                    18

<210> SEQ ID NO 5
<211> LENGTH: 18
<212> TYPE: DNA
<213> ORGANISM: Homo sapiens
<220> FEATURE:

<400> SEQUENCE: 5
ccatcaggac catcttca                                                    18

<210> SEQ ID NO 6
<211> LENGTH: 18
<212> TYPE: DNA
<213> ORGANISM: Homo sapiens
<220> FEATURE:

<400> SEQUENCE: 6
gaccaaggcg ctatgtac                                                    18

<210> SEQ ID NO 7
<211> LENGTH: 117
<212> TYPE: PRT
<213> ORGANISM: Homo sapiens
<220> FEATURE:

<400> SEQUENCE: 7

Met Ser Trp Arg Gly Arg Ser Thr Tyr Tyr Trp Pro Arg Pro Arg Arg
1               5                   10                  15

```
Tyr Val Gln Pro Gly Pro Met Arg Pro Glu Gln Phe Ser Asp Glu Val
            20                  25                  30

Pro Glu Met Ile Glu Pro Ala Thr Pro Glu Glu Gly Glu Pro Ala Thr
            35                  40                  45

Gln Arg Gln Asp Pro Ala Ala Ala Gln Glu Gln Glu Asp Glu Gly Ala
    50                  55                  60

Ser Ala Gly Gln Gly Pro His Pro Gln Thr Gly Lys Pro Glu Ala His
65                  70                  75                  80

Ser Gln Glu Gln Gly Cys Glu Cys Glu Asp Gly Pro Asp Gly Gln Glu
                85                  90                  95

Met Asp Pro Pro Asn Pro Glu Glu Val Lys Thr Pro Glu Glu Gly Glu
                100                 105                 110

Lys Gln Ser Gln Cys
            115

<210> SEQ ID NO 8
<211> LENGTH: 116
<212> TYPE: PRT
<213> ORGANISM: Homo sapiens
<220> FEATURE:

<400> SEQUENCE: 8

Met Ser Trp Arg Gly Arg Ser Thr Tyr Arg Pro Arg Pro Arg Arg Tyr
1               5                   10                  15

Val Glu Pro Pro Glu Met Ile Gly Pro Met Arg Pro Glu Gln Phe Ser
            20                  25                  30

Asp Glu Val Glu Pro Ala Thr Pro Glu Glu Gly Glu Pro Ala Thr Gln
            35                  40                  45

Arg Gln Asp Pro Ala Ala Ala Gln Glu Gln Glu Asp Glu Gly Ala Ser
    50                  55                  60

Ala Gly Gln Gly Pro Lys Pro Glu Ala Asp Ser Gln Glu Gln Gly His
65                  70                  75                  80

Pro Gln Thr Gly Cys Glu Cys Glu Asp Gly Pro Asp Gly Gln Glu Met
                85                  90                  95

Asp Pro Pro Asn Pro Glu Glu Val Lys Thr Pro Glu Glu Lys Glu Lys
                100                 105                 110

Gln Ser Gln Cys
            115

<210> SEQ ID NO 9
<211> LENGTH: 9
<212> TYPE: PRT
<213> ORGANISM: Homo sapiens
<220> FEATURE:

<400> SEQUENCE: 9

Glu Gly Glu Pro Ala Thr Gln Arg Gln
                5

<210> SEQ ID NO 10
<211> LENGTH: 9
<212> TYPE: PRT
<213> ORGANISM: Homo sapiens
<220> FEATURE:

<400> SEQUENCE: 10

Tyr Tyr Trp Pro Arg Pro Arg Arg Tyr
                5
```

<210> SEQ ID NO 11
<211> LENGTH: 9
<212> TYPE: PRT
<213> ORGANISM: Homo sapiens
<220> FEATURE:

<400> SEQUENCE: 11

Arg Tyr Val Gln Pro Pro Glu Met Ile
                 5

<210> SEQ ID NO 12
<211> LENGTH: 9
<212> TYPE: PRT
<213> ORGANISM: Homo sapiens
<220> FEATURE:

<400> SEQUENCE: 12

Ile Gly Pro Met Arg Pro Glu Gln Phe
                 5

<210> SEQ ID NO 13
<211> LENGTH: 9
<212> TYPE: PRT
<213> ORGANISM: Homo sapiens
<220> FEATURE:

<400> SEQUENCE: 13

Trp Pro Arg Pro Arg Arg Tyr Val Gln
                 5

<210> SEQ ID NO 14
<211> LENGTH: 8
<212> TYPE: PRT
<213> ORGANISM: Homo sapiens
<220> FEATURE:

<400> SEQUENCE: 14

Tyr Pro Pro Met Ile Gly Pro Met
                 5

<210> SEQ ID NO 15
<211> LENGTH: 10
<212> TYPE: PRT
<213> ORGANISM: Homo sapiens
<220> FEATURE:

<400> SEQUENCE: 15

Met Ser Trp Arg Gly Arg Ser Asp Glu Val
                 5                  10

<210> SEQ ID NO 16
<211> LENGTH: 9
<212> TYPE: PRT
<213> ORGANISM: Homo sapiens
<220> FEATURE:

<400> SEQUENCE: 16

Arg Pro Glu Gln Phe Ser Asp Glu Val
                 5

<210> SEQ ID NO 17
<211> LENGTH: 9
<212> TYPE: PRT
<213> ORGANISM: Homo sapiens
<220> FEATURE:

```
<400> SEQUENCE: 17

Asp Glu Val Glu Pro Ala Thr Pro Glu
                5

<210> SEQ ID NO 18
<211> LENGTH: 9
<212> TYPE: PRT
<213> ORGANISM: Homo sapiens
<220> FEATURE:

<400> SEQUENCE: 18

Gln Glu Gly Glu Asp Glu Gly Ala Ser
                5

<210> SEQ ID NO 19
<211> LENGTH: 9
<212> TYPE: PRT
<213> ORGANISM: Homo sapiens
<220> FEATURE:

<400> SEQUENCE: 19

Glu Glu Gly Glu Lys Gln Ser Gln Cys
                5

<210> SEQ ID NO 20
<211> LENGTH: 9
<212> TYPE: PRT
<213> ORGANISM: Homo sapiens
<220> FEATURE:

<400> SEQUENCE: 20

Met Asp Pro Pro Asn Gln Glu Glu Val
                5

<210> SEQ ID NO 21
<211> LENGTH: 9
<212> TYPE: PRT
<213> ORGANISM: Homo sapiens
<220> FEATURE:

<400> SEQUENCE: 21

Tyr Val Glu Pro Pro Glu Met Ile Gly
                5

<210> SEQ ID NO 22
<211> LENGTH: 9
<212> TYPE: PRT
<213> ORGANISM: Homo sapiens
<220> FEATURE:

<400> SEQUENCE: 22

Thr Tyr Arg Pro Arg Pro Arg Arg Tyr
                5

<210> SEQ ID NO 23
<211> LENGTH: 9
<212> TYPE: PRT
<213> ORGANISM: Homo sapiens
<220> FEATURE:

<400> SEQUENCE: 23

Arg Tyr Val Glu Pro Pro Glu Met Ile
                5

<210> SEQ ID NO 24
```

-continued

```
<211> LENGTH: 9
<212> TYPE: PRT
<213> ORGANISM: Homo sapiens
<220> FEATURE:

<400> SEQUENCE: 24

Arg Pro Arg Pro Arg Arg Tyr Val Glu
                5

<210> SEQ ID NO 25
<211> LENGTH: 9
<212> TYPE: PRT
<213> ORGANISM: Homo sapiens
<220> FEATURE:

<400> SEQUENCE: 25

Glu Pro Pro Glu Met Ile Gly Pro Met
                5

<210> SEQ ID NO 26
<211> LENGTH: 8
<212> TYPE: PRT
<213> ORGANISM: Homo sapiens
<220> FEATURE:

<400> SEQUENCE: 26

Tyr Arg Pro Arg Pro Arg Arg Tyr
                5

<210> SEQ ID NO 27
<211> LENGTH: 9
<212> TYPE: PRT
<213> ORGANISM: Homo sapiens
<220> FEATURE:

<400> SEQUENCE: 27

Tyr Tyr Trp Pro Arg Pro Arg Arg Tyr
                5
```

ISOLATED GAGE-7B AND 8 PROTEINS

This application is a divisional application of U.S. Ser. No. 09/163,748 filed Sep. 30, 1998 (now U.S. Pat. No. 6,509,172).

FIELD OF THE INVENTION

This invention relates to a nucleic acid molecule which codes for a tumor rejection antigen precursor. More particularly, the invention concerns genes, whose tumor rejection antigen precursor is processed, inter alia, into at least one tumor rejection antigen that is presented by MHC molecules. The genes in question are members of the GAGE family of genes.

BACKGROUND AND PRIOR ART

The process by which the mammalian immune system recognizes and reacts to foreign or alien materials is a complex one. An important facet of the system is the T lymphocyte, or "T cell" response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology*; (J.P. Lipincott Company, 1987), especially chapters 6-10. The interaction of T cells and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992). Also see Engelhard, Ann. Rev. Immunol. 12: 181-207; (1994).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs cytolytic T lymphocytes, or "CTLs" hereafter. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also, see U.S. Pat. No. 5,342,774.

In U.S. Pat. No. 5,405,940, the disclosure of which is incorporated by reference, it is explained that the MAGE genes code for proteins which are processed to nonapeptides which are then presented by an HLA-A1; molecule. The reference teaches that given the known specificity of particular peptides for particular HLA molecules, one should expect a particular peptide to preferably bind to one HLA molecule. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. Pat. No. 5,629,166; filed incorporated by reference, the fact that the MAGE-1; expression product is processed to a second TRA is disclosed. This second TRA is presented by HLA-C clone 10; molecules. The disclosure shows that a given TRAP can yield a plurality of TRAs. Also, see U.S. Pat. No. 5,554,506, incorporated by reference, teaching peptides which bind to HLA-A2.

U.S. Pat. Nos. 5,530,096; and 5,487,934; incorporated by reference herein teach that tyrosinase, a molecule which is produced by some normal cells (e.g., melanocytes), is processed in tumor cells to yield peptides presented by HLA-A2; molecules.

In U.S. patent application Ser. No. 08/032,978, filed Mar. 18, 1993 (now U.S. Pat. No. 5,620,886), and incorporated by reference in its entirety, a second TRA, not derived from tyrosinase is taught to be presented by HLA-A2 molecules. The TRA is derived from a TRAP, but is coded for by a non-MA GB gene. This disclosure shows that a particular HLA molecule may present TRAs derived from different sources.

In U.S. Pat. No. 5,571,711, filed Jun. 17, 1993 and incorporated by reference herein, an unrelated tumor rejection antigen precursor, the so-called "BAGE" precursor, is described. The BAGE precursor is not related to the MAGE family.

A futher family of genes which are processed into tumor rejection antigens is taught by U.S. Pat. Nos. 6,610,013 and 5,648,226, as well as patent applications Ser. Nos. 08/531,662 and 08/602,039, filed on Sep. 21, 1995 and Feb. 15, 1996 respectively, now U.S. Pat. Nos. 5,858,689 and 6,069,001 respectively, and U.S. patent applications Ser. No. 08/669,161 (now U.S. Pat. No. 6,013,481) and Ser. No. 09/012,818, filed on Jun. 24, 1996 and Jan. 23, 1998, respectively. All of these applications are incorporated by reference. They reveal that there is a family of genes, the "GAGE" genes, which are related to each other. Six members of the GAGE family are described in these references.

It has now been found that there are at least two further members of the GAGE family, referred to hereafter as GAGE-7 and GAGE-8. These genes, as well as other aspects of the inventions, will be described in detail in the disclosure which follows.

DETAILED DESCRIPTION OF PREFERRED EMBODIMENTS

Example 1

Melanoma cell line MZ2-MEL and cell lines derived therefrom are known. See, e.g., U.S. Pat. No. 5,342,774, incorporated by reference. One subclone, i.e., MZ2-MEL 3.0 was obtained by limiting dilution, and is described in the '774 patent. A subline, i.e., MZ2-ME2.43 was derived by limiting dilution of MZ2-MEL 3.0 cells which had survived mutagen treatment. See Herin, et al, Int. J. Canc. 39:390-396 (1987); Van den Eynde, et al, Int J. Canc. 44:634-640 (1980). This subline had been used as a source of cDNA from which nucleic acid molecules encoding GAGE 1-6 were isolated. See U.S. Pat. Nos. 5,610,013; 5,648,226; application Ser. Nos. 08/531,662; 08/602,039; 08/669,661;; and 09/012,818 cited supra, and Van den Eynde, et al, J. Exp. Med. 182:689-698 (1995), all of which are incorporated by reference.

The cDNA library from MZ2-MEL.43 was rescreened, using the same protocols as are set forth in the above referenced patent and 1995 paper. Two additional positive clones were identified. These molecules were named GAGE-7B and GAGE-8. They are discussed further, infra. The nucleotide sequences for cDNA for these molecules are set forth as SEQ ID NO: 1 (GAGE-8), and SEQ ID NOS: 2 and 3 (GAGE-7B).

Example 2

These experiments describe the isolation of genomic DNA molecules encoding GAGE-7B.

Peripheral blood lymphocytes (PBLs) were isolated, and grown, using standard methodologies. The genomic DNA was then isolated from the PBLS, partially digested with endonuclease Sau3A1, size fractionated using NaCl density gradient centrifugation, and then ligated into GEM-11; cloning vector, which had been digested with BamHI and EcoRI.

The phage library was screened, using a probe labeled with $\alpha^{32}P$ dCTP, consisting of nucleotides 18-309 of cDNA for GAGE-1. Conditions for this Southern hybridization was standard, as described by Sambrook et al: Molecular Cloning: A Laboratory Manual (Cold Spring Harbor Press, 1989), incorporated by reference. The washing conditions were 0.2× SSC, 0.1% SDS, at 65° C.

One of the positive clones was analyzed, and found to contain an insert corresponding to GAGE-7B. The sequence, set forth at SEQ ID NO:3, contains 5 exons, including an open reading frame over exons 2 to 5, which encodes a 117 amino acid product.

The fourth intron of this sequence includes two regions which show strong homology with a region found only in GAGE-1. There is a 561 base pair segment positioned in between these regions at nucleotides 7109-7659, which corresponds to a truncated, L1 retroposon which belongs to the family of long interspersed repeated elements, or "LINE"; as described by Hutchinson, et al, in Berg, et al, eds, "Mobile DNA" (Am. Soc. Microbiol. 1989), incorporated by reference. The LINE element is flanked by a perfect 13 base pair target site duplication, and contains part of the reverse transcriptase coding region, the 3'-untranslated region, and the poly-A tail of the original retroposon.

Example 3

A cosmid library was prepared using genomic DNA from renal cell carcinoma cell line LE9211-RCC, following the methodologies described by Lurquin, et al, Cell 58: 293-303 (1989), and screened using the Southern hybridization method set forth in example 2, using the same probe.

A cosmid was identified which contained genomic DNA for GAGE-8. Its structure was the same as that of GAGE-7B, including the LINE insertion discussed supra.

Example 4

These experiments describe how the chromosomal location of the GAGE genes was determined. Southern blot analysis was carried out on a panel of hamster or mouse×human somatic cell hybrids, obtained from the Human Genetic Mutant Cell Repository. The DNA from these somatic cell hybrids was isolated, digested with EcoRI, and used to prepare Southern blots, in accordance with Arden, at el, Cytogenet. Cell Genet. 53:161-165 (1990), incorporated by reference. The GAGE-1; probe, labeled with $\alpha^{32}P$ dCTP, as described supra, was used. A single, EcoRI band of 4.3 kilobases was detected, indicating that the EcoRI sites defining the fragment are conserved in all GAGE genes. The only hybridization signal came from a hybrid containing the human X chromosome. No signal came from hybrids containing human autosomes, or the Y chromosome.

Experiments were than carried out to refine the localization of the GAGE locus. Somatic cell hybrids containing only a portion of the X chromosome were analyzed via Southern hybridization, as described supra, as well as by PCR.

For PCR, primers corresponding to nucleotides 453-470 of GAGE-1; cDNA (sense), and nucleotides 613-630 of GAGE-1; cDNA (antisense), were used. These should amplify a 0.7 kb fragment of genomic DNA, and a fragment consisting of nucleotides 453-630 of GAGE-1; cDNA, as set forth in U.S. Pat. No. 5,610,013 at SEQ ID NO: 1. Thirty five cycles of amplification were carried out, each cycle consisting of denaturation at 94° C. (1 minute), annealing at 50° C. (1 minute), and extension at 72° C. for 1; minute. The PCR was preceded by 3 minutes of incubation at 94° C., and was followed by a soak at 72° C. for 10 minutes. Amplified products were electrophoresed on 2% agarose gels, and were visualized by ethidium bromide staining. The analysis revealed that the GAGE genes are located in chromosomal region Xp21-Xq13.

Example 5

A further set of experiments were carried out to find the location of the GAGE locus, using fluorescence in situ hybridization, or "FISH". To accomplish this, PBLs were stimulated with PHA, and cultured for 72 hours. Banded chromosomes were obtained by inoculating some cultures with 5-bromodeoxyuridine, in accordance with Lemieux, et al, Cytogenet. Cell Genet 59:311-312 (1992). Cytogenetic harvests, and slide preparations were prepared using standard methods. Slides were stored at −80° C. until used.

FISH hybridization to metaphase chromosomes was carried out following Pinkel, et al, Proc. Natl. Acad. Sci USA 83:2934-2938 (1986). Briefly, slides were denatured for 2 minutes in 70% formamide/2×SSC (pH 7.0), and then dehydrated in ice cold ethanol. A cosmid which contained gDNA for GAGE-7B was used as a probe. The probe (100 ng) was labeled with digoxigenin, preannealed with 100 mg of COT-1 DNA, dissolved in buffer (50% formamide, 2×SSC), denatured at 75° C. for 5 minutes, and then applied to slides. The probes were hybridized to the material on the slides, overnight at 37° C., in a humid chamber.

After the incubation, the slides were washed using standard procedures, and then analyzed using standard FITC-digoxigenin detection methods, together with an amplification protocol for dual color FISH. The slides were counterstained by mounting in an antifade solution containing 1; mg/ml phenylenediamine and 0.3 mg/ml propidium iodide. Spreads were examined, and photographed. A signal was deemed to be specific only if detected on each chromatid of a single chromosome. Chromosome identification was performed via simultaneous hybridization with the satellite repeat probe, or by R-banding, using 5-bromodeoxyuridine in accordance with Lemieux, et at, supra.

These experiments indicated that the GAGE locus is in the p11.2-p11.4 region of the X chromosome.

Example 6

These experiments were designed to determine expression of GAGE genes in various cell and tumor types. For each type of cell assayed, total RNA was extracted, using standard guanidium-isothiocyanate procedures, as taught by e.g., Davis, et al. in Basic Methods In Molecular Biology, Elsevier Science Publishing Co., New York (1986), pp. 130-135. Reverse transcription was carried out on 2 ug samples of the total RNA, using 2 mM of Oligo(dT)$_{15}$ primer, in a reaction volume of 20 ul. Portions of the resulting cDNA (1/20 of the product), were used in the PCR amplification. In order to amplify GAGE-1, 2, and 8, the primers used were:

```
                                    (sense, SEQ ID NO: 4)
    5'-GACCAAGACG CTACGTAG-3'
    and
                                    (antisense, SEQ ID NO: 5)
    5'-CCATCAGGAC CATCTTCA-3'
```

For GAGE-3, 4, 5, 6; & 7B, the primers were:
5'- GACCAAGGCG CTATGTAC-3'
(sense, SEQ ID NO: 6) and SEQ ID NO: 5

For all amplifications, the denaturation step was 94° C. for 5 minutes, then 30 cycles of amplification (1 minute at 94° C., 2 minutes at 58° C., 2 minutes at 72° C.), then a final extension step of 72° C. for 15 minutes. The products were analyzed by agarose gel electrophoresis, with RNA integrity being checked by reverse transcription and amplification of β-actin mRNA.

When these primers are used, SEQ ID NOS: 4 and 5 produce a fragment consisting of nucleotides 107-350 of SEQ ID NO: 1. SEQ ID NOS: 5 and 6 produce a fragment consisting of nucleotides 92-335 of SEQ ID NO: 2.

Table 1, which follows, shows the results. The highest fraction of positive tumors were found in melanoma, esophageal and lung carcinomas. GAGE 1, 2 and 8 was found in prostate carcinomas, breast carcinomas, and sarcomas. GAGE 3, 4, 5, 6 and 7B were not found in these tumors. No expression of GAGE was found in colorectal and renal carcinoma.

noma cell lines. All GAGE genes were found to be expressed following treatment of PHA stimulated PBLs.

The foregoing examples set forth the invention, which includes isolated nucleic acid molecules which encode proteins GAGE 7B and GAGE 8. These may be, e.g., those set forth at SEQ ID NO: 1, 2 or 3, as well as all nucleic acid molecules which encode the proteins encoded by theses sequences. When GAGE-7B and GAGE-8; are compared to the other members of the GAGE family, cDNA for GAGE-8 is found to be identical to cDNA for GAGE-2 but for a single nucleotide, at nucleotide 268 ("C" in GAGE-2, versus "G" in GAGE-8). This leads to a change in the amino acid at position 74 (His in GAGE-2, Asp in GAGE-8). GAGE-7B is identical to GAGE-4, but for two nucleotides at positions 268 and 548. This first difference ("G" in GAGE-4, "C" in GAGE-8), results in a change at amino acid 74 as well (Asp in GAGE-4, His in GAGE-7B).

There are further differences in the organization of the genomic DNA, as explained supra. Specifically, GAGE-8 and GAGE-7B differ from GAGEs 2-6 in that they contain two inserts in the fourth intron. These inserts are found in GAGE-1 genomic DNA; however, GAGE-8 and 7B also contain a 561 base pair insert positioned in between these two inserts, which is not found in the genomic DNA of GAGE-1.

In addition to the nucleic acid molecules discussed supra, other features of the invention include expression vectors which include the nucleic acid molecules of the invention, operably linked to a promoter. Both cDNA and genomic DNA can be used, in expression vectors of various types. These, as well as the isolated nucleic acid molecules of the invention, can be used to make recombinant eukaryotic and prokaryotic cells, which contain either the isolated nucleic acid molecules or the expression vectors of the invention. The choice of which nucleic acid molecule or which expression vector to use will be up to the skilled artisan, depending upon the application of interest.

TABLE 1

Expression of the GAGE genes in tumors

| | Number of samples ALL GAGE | | | | | | |
|---|---|---|---|---|---|---|---|
| Tumor | tested | Expression of GAGE-1,2,8* Expression of GAGE-3,4,5,6,7B | 1,2,8 + + | 3-6 +7B − + | None − − | % of samples expressing GAGE-1,2,7 and/or GAGE-3,4,5,6,8 | |
| Cutaneous melanoma (primaries) | 79 | | 22 | 1 | 10 | 46 | 42% |
| Cutaneous melanoma (metastases) | 211 | | 79 | 8 | 26 | 98 | 54% |
| Esophageal squamous cell carcinoma | 18 | | 7 | 1 | 1 | 9 | 50% |
| Esophageal adenocarcinoma | 5 | | 1 | 0 | 0 | 4 | 20 |
| Lung squamous cell carcinoma | 83 | | 28 | 4 | 7 | 44 | 47 |
| Lung adenocarcinoma | 42 | | 13 | 2 | 6 | 21 | 50 |
| Head & neck carcinoma | 92 | | 21 | 3 | 5 | 63 | 31 |
| Bladder carcinoma (superficial) | 35 | | 1 | 0 | 0 | 34 | 3 |
| Bladder carcinoma (infiltrating) | 40 | | 8 | 2 | 6 | 24 | 40 |
| Leukemia | 76 | | 0 | 0 | 3 | 73 | 4 |

Example 7

In order to determine if expression of GAGE genes could be induced by demethylation, samples of cultured tumor and normal cells were incubated for 72 hours in culture medium containing 1 uM 5-aza-2'-deoxycytidine. SEQ ID NOS: 4 and 5, supra, were used in the amplification protocol. GAGE 1, 2, and 8 were found to have been induced in sarcoma and mela- The nucleic acid molecules of the invention do include segments which correspond to peptides presented by HLA-Cw6 and HLA-A29, i.e., YRPRPRRY (GAGE 1, 2 and 8), and YYWPRPRRY (GAGE 3, 4, 5, 6 and 7B). Hence, a further aspect of the invention are recombinant cells which, in addition to including molecules which encode GAGE-7B and GAGE-8, also include one or more nucleic acid molecules which encode MHC molecules, such as HLA-Cw6 and/or HLA-A29. It is to be understood that additional genes which are processed to presented antigens may be used as well the GAGE 7B and 8 genes.

Also a feature of the invention are the proteins encoded by the nucleic acid molecules of the invention. As explained, supra, these proteins are similar, but not identical to other GAGE proteins. Also, part of the invention are fragments of the proteins of the invention. In particular, these fragments compare at least the first 74 amino acids encoded by the SEQ ID NO: 1, 2 or 3, and no more than the entire molecule encoded by these sequences. These proteins are set forth at SEQ ID NOS.: 7 and 8. Also a part of the invention are those peptides, derived form GAGE 7B and/or GAGE 8, which complex to MHC molecules, thereby identify a particular molecule, and also in at least some cases, facilitating the proliferation of cytolytic T cells which recognize complexes of the peptide and the MHC molecule to which it binds. One or more of these peptides can be combined in compositions, which may also include one or more adjuvants, such as GM-CSF, an interleukin, an emulsifying oil such as Vitainin E, a saponin, etc.

"Minigenes" can also be produced which are nucleic acid molecules that consent of nucleotides that encode these peptides. Constructs can also be prepared, such as expression vectors, which encode one or more of these peptides.

An exemplary list of such peptides, with the partner MHC molecule, follows:

GAGE 7B

| Position | Sequence | HLA Molecule |
| --- | --- | --- |
| 43-51 | EGEPATQRQ | A1 |
| 9-17 | YYWPRPRRY | A24 |
| 16-24 | RYVQPPEMI | A24 |
| 24-32 | IGPMRPEQF | A24 |
| 11-19 | WPRPRRYVQ | B7 |
| 19-27 | QPPEMIGPM | B7 |
| 11-19 | WPRPRRYVQ | B8 |
| 1-9 | MSWRGRSTY | B3501 |
| 19-27 | QPPEMIGPM | B3501 |
| 28-36 | RPEQFSDEV | B3501 |
| 1-9 | MSWRGRSTY | B4403 |
| 33-41 | DEVEPATPE | B4403 |

GAGE 7B -continued

| Position | Sequence | HLA Molecule |
| --- | --- | --- |
| 56-64 | QEGEDEGAS | B4403 |
| 108-116 | EEGEKQSQC | B4403 |
| 16-24 | RYVQPPEMI | B5201 |
| 19-27 | QPPEMIGPM | B5201 |
| 24-32 | IGPMRPEQF | B5201 |
| 28-36 | RPEQFSDEV | B5201 |
| 97-105 | MDPPNPEEV | B5201 |
| 19-27 | QPPEMIGPM | Cw0602 |
| 28-36 | RPEQFSDEV | Cw0602 |

GAGE 8

| Position | Sequence | HLA Molecule |
| --- | --- | --- |
| 16-24 | YVEPPEMIG | A1 |
| 42-50 | EGEPATQRQ | A1 |
| 8-16 | TYRPRPRRY | A24 |
| 15-23 | RYVEPPEMI | A24 |
| 23-31 | IGPMRPEQF | A24 |
| 10-18 | RPRPRRYVE | B7 |
| 18-26 | EPPEMIGPM | B7 |
| 1-9 | MSWRGRSTY | B3501 |
| 18-26 | EPPEMIGPM | B3501 |
| 27-35 | RPEQFSDEV | B3501 |
| 1-9 | MSWRGRSTY | B4403 |
| 33-41 | DEVEPATPE | B4403 |
| 56-64 | QEGEDEGAS | B4403 |
| 108-116 | EEGEKQSQC | B4403 |
| 18-26 | EPPEMIGPM | Cw0602 |
| 27-35 | RPEQFSDEV | Cw0602 |

Other features of the invention will be clear to the skilled artisan, and will not be set forth here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

GAGE-8 cDNA

```
  1 ctgtgaggca gtgctgtgtg gttcctgccg tccggactct ttttcctcta ctgagattca 61 tctgtgtgaa atatgagttg gcgaggaaga tcgacctatc ggcctagacc aagacgctac 121 gtagagcctc ctgaaatgat tgggcctatg cggcccgagc agttcagtga tgaagtggaa 181 ccagcaacac ctgaagaagg ggaaccagca actcaacgtc aggatcctgc agctgctcag 241 gagggagagg atgagggagc atctgcaggt caagggccga agcctgaagc tgatagccag 301 gaacagggtc acccacagac tgggtgtgag tgtgaagatg gtcctgatgg gcaggagatg 361 gacccgccaa atccagagga ggtgaaaacg cctgaagaag gtgaaaagca atcacagtgt 421 taaagaaga cacgttgaaa tgatgcaggc tgctcctatg ttggaaattt gttcattaaa 481 attctcccaa taaagcttta cagccttctg caaagaaaaa aaaaaaaaa
```

| GAGE 7B cDNA |
|---|
| 1 tggttcctgc cgtccggact cttttttcctc tactgagatt catctgtgtg aaatatgagt |
| 61 tggcgaggaa gatcgaccta ttattggcct agaccaaggc gctatgtaca gcctcctgaa |
| 121 atgattgggc ctatgcggcc cgagcagttc agtgatgaag tggaaccagc aacacctgaa |
| 181 gaagggaac cagcaactca acgtcaggat cctgcagctg ctcaggaggg agaggatgag |
| 241 ggagcatctg caggtcaagg gccgaagcct gaagctcata gccaggaaca gggtcaccca |
| 301 cagactgggt gtgagtgtga agatggtcct gatgggcagg agatggaccc gccaaatcca |
| 361 gaggaggtga aaacgcctga agaaggtgaa aagcaatcac agtgttaaaa gaaggcacgt |
| 421 tgaaatgatg caggctgctc ctatgttgga aatttgttca ttaaaattct cccaataaag |
| 481 ctttacagcc ttctgcaaag aaaaaaaaaa aaaaaaaaa aaaaaa |

| GAGE7B gDNA |
|---|
| 1 gagctcgctg cagccttgac ctcctgggct caagcgctcc tcccacctca gcctcctgag |
| 61 tagctgtgag tataggtaca tgccaccatg cncagctaat ttttcgatgg ttttttttgtt |
| 121 tgttttttgt agtgatgaga ttttctgatg ttgcttaggc tggtctcgaa gtcctgagct |
| 181 caggtgatct ggccagctca gcctcccaaa atactaggat tacaggcgtg anttggcctg |
| 241 gtctggtttt tcttatatag gggtcttatc tatataaaga ctaaagttaa tctgtgcctt |
| 301 tgtgcgggtg ggctaagagc atgatgactt ttatcattct attgatttaa agaaaactgt |
| 361 ccttgactta ccagtgtgta agtccatgaa agcataattc tgttgaaagc atatattgtt |
| 421 aatgggtgtt gggaaccgtg cactttccgc tgctgtggga gcatgtcctt ggaggtacct |
| 481 ttcatctgtt ttctcaactc caaacatctt aggaccatgg ttgtgactg gtaggactat |
| 541 gtatcttgct gctttcaaga cggagtatat tttcacgtgg tgtcactctg gctgtcctgt |
| 601 ttccctaata ctgtcacttc accctctgcg attctgatgc tacaaatgat agatatcgtt |
| 661 ttagcatttt cttacgggtc ctagcgattc tattcatttt tctttcagtc tctttctctg |
| 721 acttgttcac attgaacaat ttccttttgg gataggttgc tatttctgtt ttcgcaggtg |
| 781 gtttacctgt cttcccagcc agtcacagtg gtccttgtcc ccatggtggg tccggggcaa |
| 841 gagagggccc tgggttgggg gtggggttca gttgaagatg gggtgagttt tgaggggagc |
| 901 actacttgag tcccagaggc ataggaaaca gcagagggag gtgggattcc cttatcctca |
| 961 atgaggatgg gcatggaggg tttggggcgt ggcgctggga acggcagccc tccccagccc |
| 1021 acagccgcgc atgctccctg ntcccgcctc agtgcgcatg ttcactgggc gtattctgcc |
| 1081 cggcccttc gcccacgtga agaacgccag ggagctgtga ggcagtgctg tgtggttcct |
| 1141 gccgtccgga ctctttttcc tctactgaga ttcatctggt aggtgtgcag gccagtcatc |
| 1201 ccggggggctg aagtgtgagt gagggtggag agggcctcgg gtgggtcagg cgggtccgtt |
| 1261 cctggtctgt ggcctccgag ggagaagggc cacgaggtta cgtacctcct tacccttcac |
| 1321 aggctgcgag gccaccggcg gcttcgtggt cgtgaagggg cctggacggg gaggaaggtg |
| 1381 ggccgtggag gggaggctgt caggggctca ggtgaagacg gggtgagtgc tgttggggg |
| 1441 atggaagtcc cgaggtgccg ggatccccga cgacacaggg cagattccct gaatgggccc |
| 1501 ggcgggggcg aggcgggcgg tgaagaaggg gcctggcacc tgggaaggct gcggcctggc |

-continued

| GAGE7B gDNA |
|---|

```
1561 gagcgccccc cccagcggtg tggagtgcgg agcgcccgag tgagaagcac tgcaaggtct
1621 cacctccgcc atggaaggtc cgaaaacagt gggaaggagt gggcgaggca gtgcggtcca
1681 accaaacttg ttgtgagggg gggtgaatgg ctctaggaag tgggagtgtg cccaaagcag
1741 caatcacgag aattgtgatt cactagggtt ttcgtgggga gtgcacttgt gaaactaaac
1801 ctcatcagaa atgacctctg tctgcggggc gcagtggcgc tcgcctacgt agtcccagtt
1861 actggggaca ctgaggtggg aggatccctt gagcgggagg tcgaggctgc agtgagctgt
1921 gatcacgccg ctgcactcca gcctgagcaa cacagcgata ccgcgtgtcc aaaagaaatt
1981 tagaaaaaaa tgtcctctgc cttttgccac acgccttaag atgattgctc tgccagcctg
2041 gccagcagaa gtggctttgt aggcactcag acagcgtaca cacgtatgct taactctggg
2101 acttattttg agagtatttt caaaagtaaa acggaaagtt aacatttatc catggaagtg
2161 atcgaatata gcagccctgt ggagcgcacg ttcccaatca cggttgtctg ttttcagtgt
2221 gaaatatgag ttggcgagga agatcgacct attattggcc tagaccaagg cgctatgtac
2281 agcctcctga aatgattggg cctatgcggg tgagtgctta acgttaatt cgatgttttc
2341 tattagtaga aattaatttt tgtgatagcg tcgttgcatt agtgtggaaa tgctgataaa
2401 ggtctttcct gctcataaaa aatgaggatg gcatctcatg aaggaaacat tgattctgga
2461 ggatttttt ttttcctctc gtgttcttca gcttttgccc atgacttctt tctccggctt
2521 tgtttgttaa tgacagattg tacacatgta ttccaacaca gagtataata gccccaaag
2581 tcctcgtgcg tcactttct cacagtaacc tccctgtggg tggagtaacc ttattgggca
2641 tagagcatag agttggagaa atgtctttag gcttagttag gaccagaaat agctatgtat
2701 tctgtgtata tatgtaaaat tttgtatcaa taacgaaact tatttttat ttgcacaccc
2761 acacgtattc cccagcccga gcagttcagt gatgaagtgg aaccagcaac acctgaagaa
2821 ggggaaccag caactcaacg tcaggatcct gcagctgctc aggagggaga ggatgaggga
2881 gcatctgcag gtcaaggtga gggaaaggga agaagaacgt ctgctggtgt gtgcgtgtgt
2941 gtgtgttcgt gtgtgtgtgt gcacgtgtgt gtgtgttagg cattgtcaca taggaggaag
3001 aggaggaaag aaaacaatgg aaagaatgcc tgaaattgac tggaaaagcg aggaggctat
3061 gtagtttgca gcttagctta ggcaaatccc tcactatgat aaaagttctc gactttatga
3121 atgagagaat ggaggtgcca ggattgtgtg ttatccaaga acccttgact ggtgaataca
3181 acatttgtac tgtgttctaa ggtttgtgtc ttoctatcat gtatgttgct ggaaagaagg
3241 aagtgatttt gctgaaaatg cttaaaactc aaaaggcttt actgtaaggt agcttagtac
3301 tgacccaaga atagacccag ttcagaggag caggagcagc tccaaaaacc gagtcgctga
3361 atgttggccc ccgtttcctt tgattgatat tttatatgg tacgtttgat aaaagctgga
3421 taaatgagga tactgccata caggtagctg gtttagtgat ttttctcagc ggcctttagg
3481 aggtgattaa atccttttat ggttagaaaa gcaaaacgg aattatcctg agattaacgt
3541 gagatggaaa taatttctcc gagataaaat gttttgaaag gaagcattta tgtaacggag
3601 gtcatggatt attccaggga tgcactgtta aaagttccta gaatctgact gacaacaatg
3661 cccattaatt gctgtccgcc cactccctta ttctcagtgc ggggacagta tatttctgt
3721 gattcacaaa caatgttata tttggtgctt tgttcttcac ggggttcatt tatggaatat
3781 tacctttagg accttcggac ctaaatataa cttatttga acaaagtgaa gtttctcttt
3841 accccgatag gtaatgggtg tcgtgactgt aagatttcca tagtcctcaa atccatccag
```

| GAGE7B gDNA |
| --- |
| 3901 ctaatcaatc cttcagaaac tgacattgta attgtaactg aaatcctacc cacgtggtag |
| 3961 acttcagatt tctcagctga cacacactgc tgttggtact ctagggctga atataagcat |
| 4021 tatacatgtc ctgtggttta tccttagatt gtcatttagg agaaaggtct aaagctgggc |
| 4081 tgaatgccat gcactcatag tcccagctac ttgggaggcc gaggtgagag gattgcttga |
| 4141 gtcctggagt tcaagcccag cctgggaaac acagtgagac ctcattgcta ataaataaat |
| 4201 aaatgaataa ataaataaac acataaataa attcattaaa taaataaagt tttcatggta |
| 4261 taggaaaaca cagatgcaaa gttttgtgc ctagtggctg gtaatgttgc aaacgtaact |
| 4321 ccttagtgaa ctgtaccact ttagttaaga tggtaaattt taggatatct gtatttttta |
| 4381 ccacaattgg aaattccttt cttcctaaag ttcagtgcag ttatcatata ttctttaaa |
| 4441 tttttactgt atgtatcttc aagacataac attcatgaaa aatttgcaca gaatagtaca |
| 4501 atgaactcat atactgttca tctggattca ccaattgtta gtagcctttc gcttcatagg |
| 4561 tttcacatct cttccctccg tctcttaccg tgctgcccac acactcacac acacacactc |
| 4621 acacacacat acggatatat gtttactgtt attaatgctg aattgtctcg ataaagtttc |
| 4681 agggattatg gtcctttacc ctatgtactt gagggtgtgt atatcgtcag aacaaagaga |
| 4741 aagtcatttc ttggatcatc actgcacaaa gataaaaatc aggaaattta acaatgagaa |
| 4801 aatggagtca tttaatcaca gagtgcatac tcaaatttc ccagttcccc agaaaatttc |
| 4861 ttttttcctt ttttttttct ftgttgagac ggagtctccc tctgtgggcc aggttggagg |
| 4921 gcagtagtgc gatctcggct cactgcaacc tacacctccc aggttctagg gattctcatg |
| 4981 cctcagcctc ccgtgtagct gggactacag gcgccggcca ctgcggtctt gaacttctgg |
| 5041 cctcacctgc tctgcccacc ttggcatccc aaaatgtttg gattgcaggc gtgagacccc |
| 5101 acgcccggcc cagataattt tattgatagg atttcttttt ctgatccaga gtccagttga |
| 5161 gaatcacacc ttgcatgtgc ctttcaggtg tttttagttt cctttaacct gtaatgtttc |
| 5221 cttaattttt cttgtcattc acgatacgga cattttgga gaggatagac cagttggttt |
| 5281 gcagaatatt ctgtagtttg ggcttttca tgtatttttt aaaagagttt tctcactcag |
| 5341 cgtttattgg tggctactca tgccatgtaa gagtctaagc gctaggagtg taagtgctgt |
| 5401 gagagacggg atttgagcct tgagtcattt aatacgagaa ggacaatcag aagtagaata |
| 5461 agagagaagt gcaaaggagg cagcaaagtt gtctgagggc agtcttcgga aaggaggagg |
| 5521 gtaatatttc gaacaccttg ttttcctgtt ttctgctaac ggactcctga ataatgttc |
| 5581 ctgggattct tatcaacaca tttattatta cgttagctaa agctctttat ataataatac |
| 5641 cgagagcatg aatatcattt tcttattcat attttatgtt ttactgctta aattgatacg |
| 5701 tattttttat ttttaagggc cgaagcctga agctcatagc caggaacagg gtcacccaca |
| 5761 gactgggtgt gagtgtgaag atggtcctga tgggcaggag atggacccgc caaatccaga |
| 5821 ggaggtgaaa acgcctgaag aaggtaggca atccattagg catgcacatt gtagggtgtc |
| 5881 tgtttccaca gtatcatatt gtaactctta ctatgttttt gagacggagt ctcgctctga |
| 5941 agaccaggct ggagtgcagt ggtgccatct cggctcactg gaaattctgt ctccagggtt |
| 6001 caagtgattc tcctgcctga gcctctggcg gagccgggct tacaggcatg ctccgccgcg |
| 6061 cccagctaat tgttgtattt ttagtagaga cagggttcg ttatgttgca caggttgttc |
| 6121 ccgaactcct gacctcaggt gatccacctg cctcgaccat tgaaattgcc gggattacag |

-continued

| GAGE7B gDNA |
|---|
| 6181 gcagagccac cgtgcccgac ccagcattat attttttaata acagagaggt aacaatactg |
| 6241 cgtctttagt aacagagttc ttatataaag gttatttgaa acgtagttca ggccccagca |
| 6301 cccggctgat agactgtcag atagggaaac aaagtgagtc aaagctatgt tgaattaaaa |
| 6361 gttttgagta taaatcctta aaccagtagc tcacaatttt cagatgcttt tgtaaaggtc |
| 6421 tgcttttaat caatacataa cacgtttgta acacccatca cttggtgtga aaaatgctga |
| 6481 agcactcatg cgggttctaa taccagctct tacagccttg gcgagattct gagtgagtcc |
| 6541 tttcccttct aaacctatct ttggttctta tgaaaatagt gagtttaagt cagagacttt |
| 6601 aaaaccattt tgcattccgt ttctttcata ctctgatcct gttgcataga atgcgtggga |
| 6661 cacagagatc atctcttcgc atggtttgtt aatcacaaat catgaaaccc tggcccgagt |
| 6721 catctgaaaa tctctgaatt gagatttcat tgtcagtaag acagtgagcg ggccctctgc |
| 6781 ttcatcctag tttttccgtg tggagagctg aatacgtagt ataagatctt tgtgaaattgt |
| 6841 gaattctccc tcttcttggt ttgtttgttt gtttgcgaca gagtctcagt gtgtcaccca |
| 6901 ggctggagtg cagtgatgca atttcagctc actgcaactt ctggctccca gctaaagccg |
| 6961 tcctcccacc tcagcctccc gagtggctgg aactacatgc acaagccacc gtgcctgact |
| 7021 acatttttt gttttcattt ttgtagagat gaggtctcac tgtgttgccc aggcagggtt |
| 7081 tctctggctt ttaatgaaca attgcttctt ttttttcctt ttatttattt attatacttt |
| 7141 aagttttagg gtacatgtga cgttgtgcag gttagttaca tacgtataca tgtgccatgc |
| 7201 tgtgcgctgc acccactatc tcatcatcta gcattaggta catctcccag tgctatccct |
| 7261 ccccccctccc cccacccgac aacagtcccc agggtgtgat attccccttc ctctgtccat |
| 7321 gtgatctcat tgttcagttc ccacctatga gtgagaatat gcggtgtttg gttttttgtt |
| 7381 cttgcgatag tttactgaga atgatgattt cnagtttcat ccatgtccct acaaaggaca |
| 7441 tgaactcttc attttttagg gctgcatagt attccatagt gtatatgtgc cacattttct |
| 7501 taatccagtc tatcgttgtt ggacatttgg gttggttcca agtctttgct atcgtgaata |
| 7561 atgccgcaat aaacatacgt gtgcaogtgt ctttatagca gcatgattta tagtcctttg |
| 7621 ggtatatacc cagtaatggg atggctgggt caaatggtac aattgcttct taaatctttc |
| 7681 cccacggaaa ccttgagtga ctgaaataaa tatcaaatgg cgagagaccg tttagttcgt |
| 7741 atcatctgtg gcatgtaggt cagtgatgct cagcatgggt gtgagtaaga tgcctgtgct |
| 7801 atgcatgctc cctgccccac tgtcagtctt catgagccac tatttctaat aagactgtag |
| 7861 acacacatac gatataatca tctctaatca tatcaaatgt tacatgtaag tttcagcttt |
| 7921 agagacatga attgataaga tttaaagttg aaagaccatg actctagtac ttcctgagta |
| 7981 atcaactgaa gtatgcttta cacatgtgtt ttccaaattg ctgactgtta attgtaagtg |
| 8041 cttgtgactt gaaaggaagc acatgatgtt cagggaggaa attccttta aattctgcag |
| 8101 gtctacgctc aaagtttatg cagaggttca attgcgtgta agacacggga tcacccatag |
| 8161 ggttctgttt ttagtccatt taataaaacc caaactgtag tgtgctttgt atgcctttag |
| 8221 ggtcatctga ataatctgtt gctaagtcat gttcccaatc gttgtgtttc tgttacaggt |
| 8281 gaaaagcaat cacagtgtta aagaaggca cgttgaaatg atgcaggctg ctcctatgtt |
| 8341 ggaaatttgt tcattaaaat tctcccaata aagctttaca gccttctgca aagaagtctt |
| 8401 gcgcatcttt tgtgaagttt atttctagct ttttgatgct gtgaaatatg tatcattctt |
| 8461 tgaaatcgtg tatttgtaact ctctgagctg gtatgtagag acatcgttct tttttttttt |

-continued

GAGE7B gDNA

```
8521  ctttctttct tgtcctctt ttgagacgga gtcttgctct gtcgcccagg ctggagtgca
8581  gtggcgcgat ctctgctcac tgcaaccccg cctcccggat tcaagcaatt gtctgcctca
8641  gcctcccgag tagctgggat tataggcacc caccagcacg ccctggctaa gttttgtgtt
8701  tttactagag atggtttcgc atcttggccg gggtgctctt gaactcctga cctcgtgatt
8761  cacctgcctt ggcctcccaa agtgctggga ttacaggcat gcacgcctcc gcgcccggtg
8821  gagacataat tcttacatat tggttttcta tccagcggcc ttgtgaaata tgcttgtgaa
8881  ttctaaagtt tacttctagg tcgttttcag tcttcaatat acagaaacat atcatcctgg
8941  aataagagca gttttgtttc cgccattttt ttttgttttt ccttttgtac ttttttttgta
9001  gagacggggt tttgccatgt ttcccgggct gttgttgnnn ttttgagtgc aagtgatgca
9061  cccacgtcac ctcccacagt gctgggatta ctggcgtggg ccaggggcca cccgtggcgg
9121  gccccgtcgt tgccattgta aagagtttta tttccttttc tgattttatg gcattgcgca
9181  gacccacccg ttacaatggt gacagtggac atccttgtct tatccctgat gagaaaccga
9241  aaaatttcaa catttcgcca tcctattcac tctccttttt ttgtagacgg actttatcag
9301  agtgagtcat tgcattctgt tccaaatttg ctgagagtat tcatttgaat atatgttgat
9361  tttcatcaaa cagtgcatct atttcgatta ccacagcgtt ttttcccatt catgggttaa
9421  tatagtgaat tcgattgata aatttgtacg ttttttaggtt cgattattaa aacttgagac
9481  agcgtctcac tctgtcaccg aggctggagt gcggtggtgt tatcagagct c
```

The invention claim is:

1. An isolated protein which is encoded by an isolated nucleic acid molecule comprising the nucleotide sequence set fort in SEQ ID NO: 1, 2, or 3.

2. A composition which comprises the isolated protein of claim 1, and an adjuvant.

3. An isolated peptide which comprises at least the first 74 amino acids of the protein encoded by the nucleotide sequence of SEQ ID NO: 1, 2, or 3, and no more than the complete protein encoded by SEQ ID NO: 1, 2, or 3.

4. An isolated protein which is encoded by nucleotides 1-528 as set forth in SEQ ID NO: 1, or by a fragment of SEQ ID NO: 1 which consists of nucleotides 107-305 of SEQ ID NO: 1.

5. An isolated protein encoded by nucleotides 1-526 of SEQ ID NO: 2, or a fragment of SEQ ID NO: 2 which comprises at least nucleotides 92-335.

6. An isolated protein which is encoded by nucleotides 1-9531 of SEQ ID NO: 3, or a fragment of SEQ ID NO: 3 which comprises at least nucleotides 7109-7659.

7. A composition comprising the isolated peptide of claim 3, and an adjuvant.

8. A composition comprising the isolated peptide of claim 4, and an adjuvant.

9. A composition comprising the isolated peptide of claim 5, and an adjuvant.

10. A composition comprising the isolated peptide of claim 6, and an adjuvant.

11. An isolated protein consisting of an amino acid sequence encoded by nucleotides 107-350 of SEQ ID NO: 1.

12. An isolated protein encoded by nucleotides 92-335 of SEQ ID NO: 2.

13. An isolated protein encoded by nucleotides 7109-7659 of SEQ ID NO: 3.

* * * * *

UNITED STATES PATENT AND TRADEMARK OFFICE
CERTIFICATE OF CORRECTION

PATENT NO. : 7,572,885 B2  Page 1 of 1
APPLICATION NO. : 10/271617
DATED : August 11, 2009
INVENTOR(S) : De Backer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 930 days.

Signed and Sealed this

Seventh Day of September, 2010

David J. Kappos
*Director of the United States Patent and Trademark Office*